United States Patent [19]

Nagabhushan et al.

[11] Patent Number: 4,582,918

[45] Date of Patent: Apr. 15, 1986

[54] PREPARATION OF INTERMEDIATES FOR (THREO)-1-ARYL-2-ACYLAMIDO-3-FLUORO-1-PROPANOLS

[75] Inventors: Tattanahali L. Nagabhushan, Parsippany; Stuart W. McCombie, Caldwell, both of N.J.

[73] Assignee: Schering Corporation, Kenilworth, N.J.

[21] Appl. No.: 651,980

[22] Filed: Sep. 19, 1984

[51] Int. Cl.$^4$ .................. C07D 301/14; C07D 303/08
[52] U.S. Cl. .................................... 549/525; 549/551; 549/554; 549/563; 564/212; 564/219; 260/349
[58] Field of Search ......................... 549/525

[56] References Cited

U.S. PATENT DOCUMENTS 3,849,482 11/1974 Christensen et al. ............... 549/525
4,311,857 1/1982 Nagabhushan ..................... 548/478

OTHER PUBLICATIONS

Jean Bensoam et al., Tetrahedron Letters, No. 4 (1979) pp. 353–356.
Harris et al., Jour. Chem. Soc. Perkin I (1976) pp. 1612–1615.
R. Krebs, CA 78:71663q and 77:61532m.

Primary Examiner—Norma S. Milestone
Attorney, Agent, or Firm—Thomas D. Hoffman; Gerald S. Rosen; Stephen I. Miller

[57] ABSTRACT

A novel sequence of highly selective chemical reactions for conversion of 3-Aryl-2-propyn-1-ols into cis-1-Aryl-3-fluoro-1-propene and into D,L-(threo)-1-Aryl-2-acylamido-3-fluoro-1-propanols is disclosed. Preparation of D-(threo)-1-Aryl-2-acylamido-3-fluoro-1-propanol antibacterial agents including the D-(threo)-3-fluoro-3-deoxy derivatives of chloramphenicol and thiamphenicol is also disclosed.

4 Claims, No Drawings

PREPARATION OF INTERMEDIATES FOR (THREO)-1-ARYL-2-ACYLAMIDO-3-FLUORO-1-PROPANOLS

BACKGROUND OF THE INVENTION

This invention relates to a method of preparing (threo)-1-Aryl-2-acylamido-3-fluoro-1-propanols. More particularly, this invention relates to preparing D-(threo)-1-Aryl-2-acylamido-3-fluoro-1-propanol antibacterial agents, including 3-fluoro-3-deoxy derivatives of chloramphenicol and of thiamphenicol. This invention also relates to cis-1-Aryl-2-(fluoromethyl)oxiranes, intermediates in the preparation of D,L-and D-(threo)-1-Aryl-2-acylamido-3-fluoro-1-propanols and to a method of preparing such intermediates.

D-(threo)-1-Aryl(phenyl or para-and/or meta-substituted phenyl)-2-acylamido-3-fluoro-1-propanols and racemic mixtures thereof are known in the art as broad spectrum antibacterial agents useful in the treatment of gram positive, gram negative and rickettsial infections. See, for example, U.S. Pat. Nos. 4,235,892, and 4,361,557.

U.S. Pat. No. 4,311,857 discloses methods of preparing D-(threo)-1-Aryl-2-acylamido-3-fluoro-1-propanols by reaction of D-(threo)-1-Aryl-2-N-protected-amino-1,3-propanediol with dialkylaminosulfur trifluoride followed by removal of the N-protecting group and thence reaction of the resulting D-(threo)-1-Aryl-2-amino-3-fluoro-1-propanol with a lower alkanoic acid derivative. However, the method uses an optically active starting material and it would be economically desirable to provide a synthetic pathway to (threo)-1-Aryl-2-acylamido-3-fluoro-1-propanols employing racemic starting materials and delay a resolution of the racemic mixture to a late step in the process.

SUMMARY OF THE INVENTION

In its broadest aspect, the present invention provides a process for the preparation of compounds represented by formulas IVa and IVb

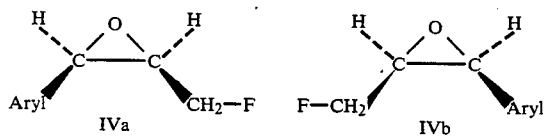

wherein Aryl is

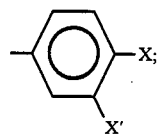

and wherein each of X and X' is independently $NO_2$, $SO_2R_1$, $SO_2NH_2$, $SO_2NHR_1$, $OR_1$, $R_1$, CN, halogen, hydrogen, phenyl or phenyl substituted by 1 to 3 halogens, $NO_2$, $SO_2R_1$ or $OR_1$; and wherein $R_1$ is lower alkyl; which comprises the following steps:

(a) contacting a 3-Aryl-2-propyn-1-ol with a fluorinating agent in an inert organic solvent to form a 1-Aryl-3-fluoro-1-propyne;

(b) contacting the product of step (a) with a reagent selective for cis-hydrogenation to form a cis-1-Aryl-3-fluoro-1-propene; and (c) contacting the product of step (b) with a peroxyacid to form the compounds represented by the formulas IVa and IVb.

The novel compounds represented by formulas IVa and IVb are cis-1-Aryl-2-(fluoromethyl)oxiranes, useful as intermediates in the preparation of D,L-(threo)-1-Aryl-2-acylamido-3-fluoro-1-propanols.

In one aspect of the present invention there is also provided a process for the preparation of D,L-(threo)-1-Aryl-2-acylamido-3-fluoro-1-propanols represented by formulas VIa and VIb

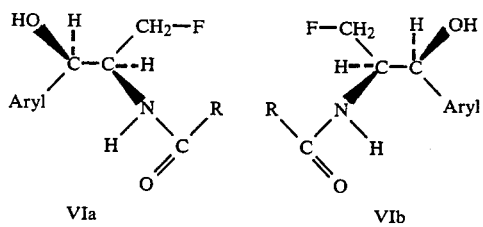

wherein R is lower alkyl or a halogenated derivative thereof; dihalogenodeuteriomethyl, 1-halogeno-1-deuterioethyl; 1-2-dihalogeno-1-deuterioethyl; azidomethyl; or methylsulfonylmethyl; wherein Aryl is

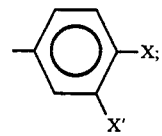

wherein each of X and X' is independently $NO_2$, $SO_2R_1$, $SO_2NH_2$, $SO_2NHR_1$, $OR_1$, $R_1$, CN, halogen, hydrogen, phenyl, or phenyl substituted by 1-3 halogens, $NO_2$, $SO_2R_1$, $R_1$, or $OR_1$; and wherein $R_1$ is lower alkyl which comprises the following steps:

(a) contacting a 3-Aryl-2-propyn-1-ol with a fluorinating agent in an inert organic solvent to form a 1-Aryl-3-fluoro-1-propyne;

(b) contacting the product of step (a) with a reagent selective for cis-hydrogenation to form a cis-1-Aryl-3-fluoro-1-propene;

(c) contacting the product of step (b) with a peroxyacid to form a cis-1-Aryl-2-(fluoromethyl)oxirane;

(d) converting the product of step (c) into D,L-(threo)-1-Aryl-2-amino-3-fluoro-1-propanol either by (i) contacting the product of step (c) with an alkali metal azide to form D,L-(threo-1-Aryl-2-azido-3-fluoro-1-propanol and then reducing the 2-azido group to a 2-amino group or (ii) contacting the product of step (c) with an imido compound to form a D,L-(threo)-1-Aryl-2-imido-3-fluoro-1-propanol and then converting the 2-imido group to a 2-amino group thereby forming D,L-(threo)-1-Aryl-2-amino-3-fluoro-1-propanols;

(e) contacting the product of step (d) with a lower alkanoic acid derivative selected from lower alkyl alkanoic acid anhydrides, lower alkyl alkanoyl halide, or a halogeno lower alkyl alkanoic acid halide or anhydride in the presence of a base, or a lower alkyl ester of an α,α-dihalogeno acetic acid or an α,α-dihalogeno propionic acid in a lower alkyl alkanol to produce the compounds of formulas VIa and VIb; and (f) recovering compounds of formulas VIa and VIb.

In a preferred embodiment of the present invention the racemic mixture of D,L-(threo)1-Aryl-2-amino-3-fluoro-1-propanols, obtained from step (d) of the process is resolved by fractional crystallization of a diastereomeric salt of D-(threo)-1-Aryl-2-amino-3-fluoro-1-propanol and an optically active acid followed by treatment of the diasteriomeric salt with aqueous base and recovery of D-(threo)-1-Aryl-2-amino-3-fluoro-1-propanol, and thence treatment of the D-threo compound with a lower alkanoic acid derivative to form the D-threo enantiomer of the compound of formula VIa.

DETAILED DESCRIPTION OF THE INVENTION

By the term "halogen" as used herein is meant, fluorine, chlorine, bromine or iodine. Fluorine and chlorine are preferred.

By the term "lower alkyl" as used herein is meant straight or branched ($C_1-C_6$) alkyl including methyl, ethyl, n-propyl, isopropyl, n-butyl, iso-butyl, tert-butyl, n-pentyl, iso-pentyl, neo-pentyl, n-hexyl, iso-hexyl. Methyl and ethyl are preferred.

By "Aryl" as used herein is meant phenyl or 4-substituted 3,4-disubstituted phenyl represented by formula

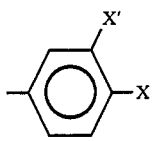

wherein each of X and X' is a member selected from the group consisting of $NO_2$, $SO_2R_1$, $SO_2NH_2$, $SO_2NHR_1$, $OR_1$, $R_1$, CN, halogen, hydrogen, phenyl and phenyl substituted by halogen, $NO_2$, $SO_2CH_3$ $R_1$ or $OR_1$ and wherein $R_1$ is methyl, ethyl, propyl or isopropyl and wherein halogen is fluorine, chlorine or bromine. Particularly interesting Aryl groups are 4-nitrophenyl (X is $NO_2$) and 4-methylsulfonylphenyl (X is $SO_2CH_3$) and 4-sulfonamidophenyl (X=$SO_2NH_2$).

The following Scheme illustrates the multistep processes of this invention for preparing cis-1-Aryl (phenyl or para- and/or meta-substituted phenyl)-(2-fluoromethyl)oxiranes and for preparing D,L-(threo) and D-(threo)-1-Aryl(phenyl or para and/or meta substituted phenyl)-2-acylamido-3-fluoro-1-propanols; and process comprises a novel sequence of highly selective chemical reactions.

SCHEME

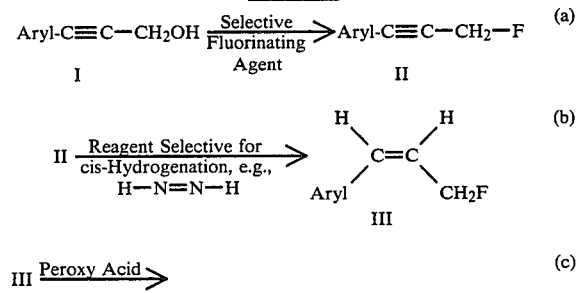

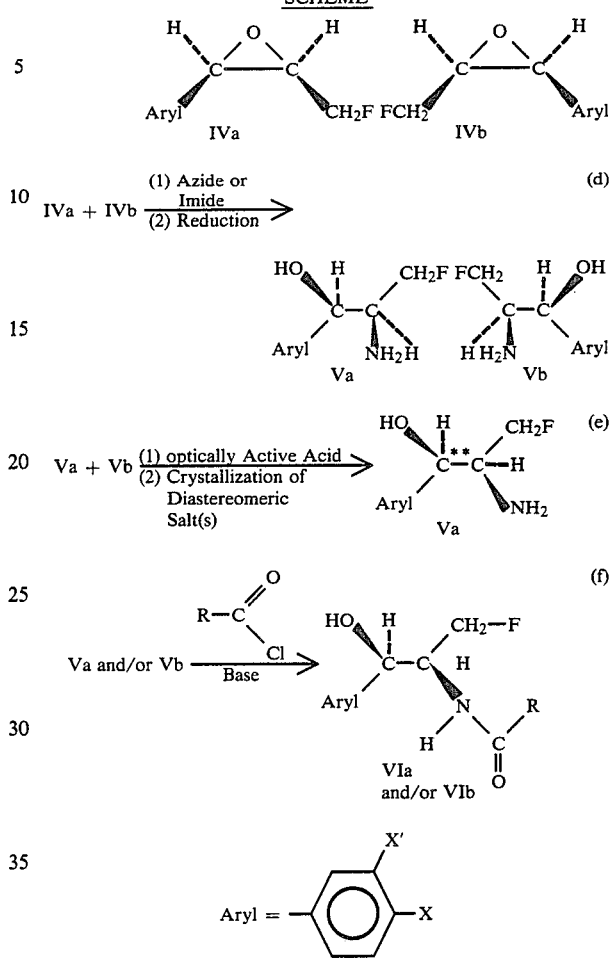

In its broadest aspect, the invention provides a process which encompasses the novel sequence of highly selective chemical reaction steps (a) to (c) in the Scheme for preparing cis-1-Aryl-2-(fluoromethyl) oxiranes.

The 3-Aryl-2-propyn-1-ols represented by formula I used as starting materials in step (a) of the processes of the present invention are either known compounds or are conveniently prepared according to known procedures. For example, 3-(4-methylsulfonylphenyl)-2-propyn-1-ol is conveniently prepared by reacting 4-bromophenyl methyl sulfone with propargyl alcohol in the presence of copper(I)iodide bis(triphenylphosphine) palladium(II)chloride and triethylamine. A general experimental procedure for preparation of 3-Aryl(phenyl or para and/or meta substituted phenyl)-2-propyn-1-ols, such as 3-(4-nitrophenyl)-2-propyn-1-ol is described by M. A. Harris et al. in *J. Chem. Soc*, Perkin I, pages 1612–1613 (1976).

In step (a) of the process depicted in the reaction Scheme, the primary hydroxy moiety in 3-Aryl-2-propyn-1-ol (compound I) is selectively converted into the corresponding primary fluoro moiety (compound 2). Suitable selective fluorinating agents include compounds with two fluorine atoms α to a nitrogen, for example $CHClFCF_2N(C_2H_5)_2$ or

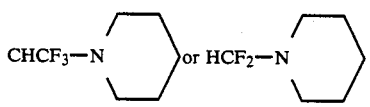

and compounds having a flourine atom attached to a hetero atom (e.g. S or P) such as $SOF_2, PF_5, SF_4, F_3S-N(C_2H_5)_2$,

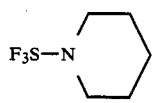

and $(C_6H_5)_3PF_2$. The preferred fluorinating agent is N-(1,1,2-trifluoro-2-chloroethyl)N, N-diethylamine, $CHClFCF_2N(C_2H_5)_2$.

The fluorinating step is conveniently carried out at temperatures in the range of about $-10°$ to about $+50°$ C., preferably about 0°–30° C. in an inert organic solvent. By "inert organic solvent" is meant any organic solvent in which compound I and the fluorinating reagents are soluble, and which is essentially inert under the reaction conditions. Dichloromethane is especially preferred.

In step (b) of the process depicted in the reaction Scheme, the 1-Aryl-3-fluoro-1-propyne represented by formula II is reduced to the cis-1-Aryl-3-fluoro-1-propene represented by formula III by use of a reagent selective for cis-hydrogenation such as diimide or hydrogen with a Lindlar catalyst, i.e., palladium precipitated on calcium carbonate and lead (II) oxide selectively poisoned by an aromatic amine, such as quinoline or pyridine in an organic solvent, e.g., ethyl acetate that dissolves at least compound II. Other reagents selective for cis-hydrogenation in the process of the present invention include a palladium-on-barium sulfate catalyst poisoned by synthetic quinoline [See D. J. Cram et al., *J. Am. Chem. Soc.*, 78, 2518 (1956)] or 5% palladium-on-barium sulfate used with pyridine as a solvent [see "Feiser and Feiser's Reagents for Organic Synthesis", Vol. 2, pages 566–569) (1969)]. The particular reagent chosen will depend upon the substituents on the phenyl ring and solubility of the compound represented by formula II as well as the ability of the reagent to effect selective cis-hydrogenation of the triple bond with a minimum of side reactions. For the selective cis-reduction of the triple bond of 1-(4-methylsulfonylphenyl)-3-fluoro-1-propyne, hydrogen and the Lindlar catalyst selectively poisoned with quinoline are preferred (see H. Lindlar et al. *Org. Syn.*, 46, 89 (1966)); for the selective cis-reduction of the triple bond of 1-(4-nitrophenyl)-3-fluoro-1-propyne, diimide is preferred (see "Fieser and Fieser's Reagents for organic Synthesis", Vol. 8, page 172, Wiley-Interscience, N.Y. 1980). Reaction conditions are not critical; generally, hydrogen pressures of about 1 atmosphere, room temperature and 1–24 hrs. are used.

In step (c) of the process depicted in the reaction Scheme, the cis-1-Aryl-3-fluoro-1-propene (compound III) is converted into the cis-1-Aryl-2-(fluoromethyl)oxiranes (compounds IVa and IVb) by use of an aliphatic or aromatic peroxyacid. Among the suitable aromatic peroxyacids are m-chloroperbenzoic acid, perbenzoic acid, and peroxyphthalic acid. Among the suitable aliphatic peroxyacid acids are peracetic acid and trifluoroperacetic acid. The preferred peroxyacid for step (c) is m-chloroperbenzoic acid. Reaction conditions are not critical. Chlorinated solvents, e.g., dichloromethane, reflux temperatures, and reaction times of 10–30 hrs are typically used. See "Feiser and Feiser's Reagents for Organic Synthesis", Vol. 9. pages 108–110.

Compounds IVa and IVb formed in step c are novel compositions of matter and may be isolated and purified by standard techniques, e.g. extraction, filtration, chromatography and crystallization. The term "Aryl" in cis-1-Aryl-2-(fluoromethyl)oxirane is defined herein above. Particularly interesting compounds represented by formulas IVa and IVb are cis-1-(4-nitrophenyl)-2-(fluoromethyl)oxirane, cis-1-(4-sulfonamidophenyl)-2-(fluoromethyl)oxirane.

When compounds IVa and IVb are used to produce the D,L- or D-(threo)-1-Aryl-2-acylamido-3-fluoro-1-propanols, process steps d+f or d+e+f are performed, respectively. Generally, it is desirable to isolate and purify compounds IVa and IVb after step (c) is performed.

In step (d) of the process depicted in the reaction Scheme, the cis-1-Aryl-2-(fluoromethyl)oxiranes (compounds IVa and IVb) are selectively converted into a racemic mixture of D,L-(threo)-1-Aryl-2-amino-3-fluoro-1-propanols (compounds Va and Vb) by use of nucleophilic nitrogen compounds in a dry aprotic solvent such as dimethylformamide or dimethyl sulfoxide at elevated temperatures (90°–120° C.) for 10–40 hrs. Typical suitable nucleophilic nitrogen compounds are alkali metal (especially Na+ and K+) imides e.g., potassium salts of phthalimide, 1,8-naphthalene dicarboximide, 5,6-norbornene dicarboximide or succinimide in combination with the free imide in a ratio of 1:4 to 0.05:4. The aroyl group, e.g., phthaloyl group is conveniently removed by treatment with hydroxylamine hydrochloride and an alkoxide base, e.g., sodium methoxide in methanol to produce the free amine. Other suitable nucleophilic nitrogen compounds include the alkali metal azides (e.g., $NaN_3$, $KN_3$) preferrably buffered with for example ammonium chloride. The azido group is reduced, conveniently with hydrogen in the presence of a catalyst, especially with hydrogen and 10% palladuim-on-charcoal at atmospheric pressure and at room temperature to give compound Va and Vb containing the free amino group. Use of either alkali metal azides or alkali metal imido compounds in combination with the free imide produces a mixture of compounds which must be purified by, for example, fractional crystallization before conversion to the free amine is effected.

In step (f) of the process depicted in the reaction Scheme, D,L- or D-(threo)-1-Aryl-2-amimo-3-fluoro-1-propanols (the mixture of compounds Va and/or Vb) is converted into the 2-acylamido derivative compounds VIa and VIb by reaction of compounds Va and/or Vb in the presence of a base and a suitable organic solvent for the reactants with a lower alkyl alkanoic acid derivative or a halogeno lower alkyl alkanoic acid halide (e.g. fluoride, chloride) or anhydride, or with a lower alkyl ester of an α,α-dihalogeno-propionic acid under reflux until the reaction goes to completion, typically in 10–20 hrs. Halogeno acetic or propionic and chlorides are preferred halogeno lower alkyl alkanoic acid halides. Typically, the base is an aliphatic amine and the organic solvent suitable for the reactants is a lower alkyl alkanol, especially methanol or ethanol or a halogenated alkane, e.g. dichloromethane. Of the lower alkyl alkanoic acid derivatives, acetic and propionic acid, chlorides and acid anhydrides are preferred. Of the lower alkyl alkyl esters of the preferred acids derivatives, the methyl and ethyl esters of the dihalogeno acetic acids and the α,α-dihalogenopropionic acids are preferred. Typical of the lower alkyl halogeno alkanoic acid derivatives are halogeno acetic and halogeno propionic acid chlorides or anhydrides, especially those substituted by one, two or three halogens (F, Cl, Br or I) including mono-,di-and trifluoro-, mono-,di-and trichloro- and mono- and dibromo- and mono-iodoacetic acid chlorides or anhydrides or esters as well as the mono-and difluoro-, the mono-and dichloro- the mono- and dibromo- and the monoiodiopropionic acid chlorides or anhydrides or esters. The halogen substituents in the propionic acid derivatives are preferably on the carbon alpha to the carbonyl function. Other typical suitable alkanoic acid derivatives are the mixed dihalogeno acetic and dihalogeno propionic acid derivatives in which both halogens are preferably bonded to the carbon alpha to the carbonyl function, e.g., fluorochloro-, fluorobromo- and chlorobromoacetic acid chlorides or anhydrides or esters as well as α-fluoro-, α-chloro- and α-bromopropionic acid chlorides or anhydrides or esters as well as trihalogenoacetic acid derivates such as dichlorofluoro- and difluorochloroacetic acid chlorides or anhydrides or esters. Additionally, suitable are those halogeno acetic and halogeno propionic acid chlorides and anhydrides and esters having a deuterio atom on the carbon alpha to the carbonyl function, e.g. dihalogenodeuterioacetic acid chlorides or anhydrides such as dichlorodeuterio difluorodeuterio- and chlorofluorodeuterioacetic acid chlorides or anhydrides or esters, as well as α,α-difluoro-α-deuterio-,α-fluoro-α-deuterio- and α,α-dichloro-α-deuteriopropionic acid chlorides, anhydrides or esters. Of the foregoing, dichloroacetic, difluoroacetic, fluorochloroacetic acid chlorides, anhydrides and the methyl and ethyl esters as well as deuterio derivatives thereof are preferred.

The racemic mixture of compounds Va and Vb resulting from step (d) of Scheme detailed above has antifungal activity. However, the preferred biologically active D-(threo)-enantiomer, compound Va, can be separated from the racemic mixture by a variety of techniques known to those skilled in the art, but preferably by fractional crystallization of the diastereomeric ammonium carboxylate salt of the D-(threo) enantiomer with an optically active acid.

The resolution step of the preferred embodiment of the process of the present invention is performed on the racemic mixture of D,L-(threo)-1-Aryl-1-2-amino-3-fluoro-1-propanols (compounds Va and Vb) prior to the step f of the process depicted in the reaction Scheme. The racemic mixture of compounds represented by formulas Va and Vb is contacted with an optically active acid, one enantiomer of which forms a crystalline diasteromeric salt with the D-(threo)-1-Aryl-2-amino-3-fluoro-1-propanol (compound Va), said salt having a higher melting point, and/or a lower solubility and/or higher crystallizability compared to that for the L-threo enantiomer. As is well known to those skilled in the art, it is advantageous to explore, on a millimole scale, the salt forming properties i.e., melting point, solubilty and crystallinity of optically active acids described in the literature in order to select the optimal resolving agent available as well as to provide crystalline diasteriomeric salts which can be used as seed crystals in resolving the racemic D,L-threo aminofluoro propanol. Generally, as is well known in the art, a resolution through separation by crystallization of diasteriomeric salts is most likely to succeed without difficulty when the acid and basic salt-forming centers of both components are proximate in space to those factors which render each asymmetric.

Typical suitable optically active acids useful for successful resolution of the racemic D,L-(threo)-1-Aryl-2-amino-3-fluoro-1-propanols are those acids represented by the formulas A and B

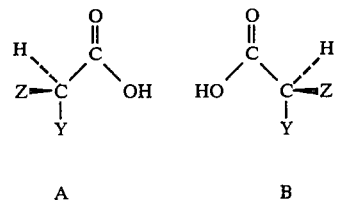

A        B wherein Z is a bulky alkyl or aromatic group such as phenyl, napthtyl, ($C_4$-$C_{10}$) branched alkyl (e.g. isobutyl, neopentyl, isohexyl, isooctyl and the like) and wherein Y is a polar group such as —$OR_2$,

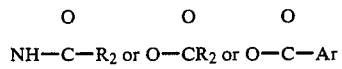

wherein $R_2$ is straight or branched ($C_1$-$C_6$)alkyl, for example, methyl, ethyl, propyls, butyls, pentyls, hexyls and wherein Ar is phenyl or para- or meta-substituted phenyl. Suitable Y groups include $CH_3O$—,$C_2H_5O$—, $C_4H_9O$—,

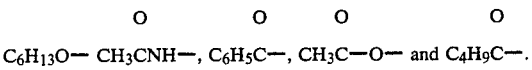

O-(+)-(S)-O-O-methylmandelic acid (formula A wherein Y=$OCH_3$ and Z=$C_6H_5$) is especially preferred.

Generally, no more than about an equivalent of the optically active acid is heated (steam bath) with the racemic D,L-(threo)-1-Aryl-2-amino-3-fluoro-1-propanols in a suitable organic solvent. The resolution is improved by seeding of the solution of racemate and optically active acid with the authentic neutral diastereomeric salt of the desired D-(threo)-1-Aryl-2-amino-3-fluoro-1-propanol and the optimal optically active acid and thereafter stirring the mixture for a short time (2 hrs). The optical rotations optical puritise of the isolated salt and the free amine are determined and the diastereomeric salt is repeatedly recrystallized to constant optically purity. When the solution of the diastereomeric salt of D-threo-1-(4-methylsulfonylphenyl)-2-amino-3-fluoro-1-propanol (compound Va wherein Aryl=4-$CH_3SO_2C_6H_4$-) and (+)-S-O-methylmandelic acid was seeded with the authentic diasteriomeric salt and stirred, the isolated salt had an optical purity of about 96% and was obtained in about 46% yield after two crystallization from n-butanol.

Among the suitable organic solvents are acetone, ethanol, ethanol-ether (1:1,v/v) and n-butanol. Use of n-butanol gave the best results (higher yield and optical purity of diastereomeric salt isolated) and is preferred. The 1:1 ethanol-ether mixture gave a diastereomeric salt with an optical purity comparable to that using n-butanol, however, in lower yield.

Compound Va can be conveniently isolated as the free amine from an aqueous solution of the diastereomeric salt by treatment of the diastereomeric salt with aqueous base, e.g., alkali metal hydroxide or carbonate and extraction of Va with an immiscible organic solvent.

EXAMPLES

General Experimental

Melting points were determined on a Fisher-Johns melting point apparatus and are uncorrectd. Infrared (ir) spectra were recorded with a Perkin-Elmer 598 spectrophotometer. The $^1$H NMR spectra were recorded with a Bruker CXP-200 (200 MHz) or a Varian-T-60 (60 MHz) spectrometer with tetramethylsilane (TMS) as the internal standard; chemical shifts are given in parts per million down field from TMS. Optical rotations were measured with a Perkin-Elmer model 141 automatic polarimeter. Thin-layer chromatography (tlc) was performed using precoated thin-layer chromatography plates (kieselgel 60 $F_{254}$, E. Merck) with a fluorescence indicator in the following solvent systems (v/v): (A) ethyl acetate-hexane (1:1); (B) ethyl acetate-hexane (3:1). Compounds were located by ultraviolet light. Preparative thin-layer chromatography was performed using precoated thin-layer chromatography plates (silica gel GF, Analtech). Column chromatography was perfomed on silica gel 60 (70–230 mesh, E. Merck). Temperatures are in degrees Celsius.

EXAMPLE 1

1-(4-Methylsulfonylphenyl)-3-Fluoro-1-Propyne

To a stirred solution of N-(1,1,2-trifluoro-2-chloroethyl)-N, N-diethylamine (6.2. g 32.5 mmol) in $CH_2Cl_2$ (20 mL) at 0°–5°, add 3-(4-methylsulfonylphenyl)-2-propyn-1-ol (4.78 g; 22.8 mmol) in $CH_2Cl_2$ (15 mL) over 10–15 min. Treat the solution with $CF_3CO_2H$ (0.2 mL) and maintain the treated solution at 20°–25° for 20 hrs.

Add methanol (5 mL) and partition the mixture in $CH_2Cl_2$-$H_2O$. Stir the organic phase 1hr with methanol (10 mL) and anhydrous $Na_2CO_3$ (10 g) [to hydrolyze any esters], filter and evaporate the organic phase. Filter the residue dissolved in $CH_2Cl_2$ through ~20 g of silica gel and elute with $CH_2Cl_2$. Evaporate all product-containing-fractions and dissolve the residue

(product + $CHClFCN(C_2H_5)_2$)

in ether (15 mL) and dilute the solution so formed slowly with hexanes (75 mL.). Refrigerate the solution and collect the product by filtration. Wash the filtered product with hexanes and dry the washed product at 25° in high vacuum to give fine white needles of the title compound, mp 97°–99° (3.25 g; 68% of theory).

$^1$H NMR ($CDCl_3$)δ:3.06 (s,3H), 5.20 (d, J=47, 2H), 7.64 (d, J=8, 2H) and 7.95 (d, J=8, 2H).

EXAMPLE 2 cis-1-(4-Methylsulfonylphenyl)-3-Fluoro-2-Propene (A) cis-hydrogenation using Lindlar catalyst and pyridine Stir a mixture of 533 mg, 2.51 mmoles of the title compound of Example 1 (recrystallized from dichloromethane-hexane), 211 mg, 2.67 mmoles of pyridine and 127 mg of Lindlar catalyst (palladium on calcium carbonate, poisoned with lead (obtained from Aldrich) in 25 mL of ethyl acetate under hydrogen at atmospheric pressure at 26° C. for 1 hr until the theoretical amount of hydrogen (62 mL) is consumed. Remove the catalyst by filtration and wash it with ethyl acetate. Wash the ethyl acetate solution successively with ice-cold 4% HCl solution, saturated $NaHCO_3$ solution and water, and dry over anhydrous $MgSO_4$. Evaporate solvent under vacuum to give the title compound as an oil (534 mg).

(B) cis-hydrogenation using Lindlar catalyst and quinoline

Shake a mixture of recrystallized title compound of Example 1 (1 g, 4.72 mmoles), quinoline (60 mg, 99% pure Aldrich) and Lindlar catalyst of procedure A of Example 2 (200 mg) in ethyl acetate (50 mL) in a Parr apparatus under hydrogen at atmospheric pressure at 30° for 20 min. or until theoretical amount of hydrogen (118 mL) is taken up. Remove catalyst by filtration and wash it with ethyl acetate. Evaporate the solvent under vacuum at 35° to give an oil. Dissolve the oil in dichlormethane (40 mL) and wash the dichloromethane solution successively with ice-cold 1 M HCl solution, saturated $NaHCO_3$ solution and water, and then dry over anhydrous $MgSO_4$. Evaporate the under vacuum to give the title compound as an oil (1 g). Purify a portion of the oil (220 mg) by column chromatography. Elute the column with ethyl acetate-hexane (1:1, v/v) to give the title compound as an oil (213 mg). The oil was 95% pure and contained 5% of the over-reduced compound 3-(4-methylsulfonylphenyl)-1-fluoropropane and had the following physical and spectral properties:

$R_f$=0.44 (solvent A); $\nu_{max}$(film): 2990, 1580 (C=C) cm$^{-1}$; $^1$H NMR ($CDCl_3$) δ: 3.06 (s, 3H), 5.06 (ddd, 2H, $J_{3,F}$=46.6 Hz, $J_{3,3'}$=6.4 Hz, $J_{3,2}$=$J_{3',2}$=1.3 Hz), 6.06 (m, 1H, $J_{2,F}$=17.3 Hz, $J_{1,2}$=12.3 Hz, $J_{2,3'}$=$J_{2,3}$=1.3 Hz), 6.70 (bd, 1H, $J_{1,2}$=12.3 Hz), 7.31 (d, 2H, J=8.3 Hz), 7.85 (d, 2H, J=8.1 Hz).

EXAMPLE 3 cis-1-(4-Methylsulfonylphenyl)-2-(fluoromethyl)oxirane

A. Reflux a solution of the title compound of Example 2 (533 mg., 2.49 mmoles), m-chloroperbenzoic acid (m-CPBA) (863 mg., 5.00 mmoles) and 3-tert-butyl-4-hydroxy-5-methylphenylsulfide (an inhibitor, 30 mg., Aldrich) in dry dichloromethane (20 mL) ($P_2O_5$ dried) for 17 hrs. Add another portion of m-CPBA (400 mg.) and reflux the solution for an additional 5 hrs. Cool the solution to room temperature, and wash the cooled solution with saturated sodium bicarbonate solution (20 mL) and add thereto sodium sulfite ($Na_2SO_3$,3 g.). Stir the resulting mixture for 30 min. Separate the organic layer and extract the aqueous layer with dichloromethane (20 mL). Wash the combined organic extract with water and dry over anhydrous $MgSO_4$. Evaporate the solvent under vacuum to give a syrup. Chromatograph the syrup on two preparative tlc plates using ethyl acetate-hexane (1:1 v/v ). Extract the bands containing the product with ethyl acetate to give the title compound, a solid (473 mg., 83% of theory). Recrystallized the solid from dichloromethane-ether;

m.p. 91°–93° C., $R_f$=0.33 (solvent A); $\nu_{max}$ (KBr): 3000, 1596 (C=C) cm$^{-1}$; $^1$H NMR ($CDCl_3$) δ:3.07 (s, 3H), 3.63 (m, 1H, $J_{2,F}=7.6$ Hz, $J_{2,1}=4.2$ Hz, $J_{2,3}=4.7$ Hz, $J_{2,3'}=6.4$ Hz), 4.22 (ddd, 1H, $J_{3,F}=47.5$ Hz, $J_{3,3'}=10.6$ Hz, $J_{3,2}=6.4$ Hz), 4.30 (dd, 1H, $J_{1,2}=4.2$ Hz, $J_{1,F}=2.1$ Hz), 4.33 (ddd, 1H, $J_{3',F}=46.8$ Hz, $J_{3',3}=10.6$ Hz, $J_{3',2}=4.7$ Hz), 6.87 (d, 2H, J=8.1 Hz), 7.96 (d, 2H, J=8.7 Hz).

B. More conveniently, isolate the title compound (2.78 g., 68%) by direct crystallization from dichloromethaneether of the reaction mixture from the m-CPBA peroxidation of 3.84 g of the cis-1-(4-Methylsulfonylphenyl)-3-fluoro-2-propene.

EXAMPLE 4

D,L-(threo)-1-(4-Methylsulfonylphenyl)-2-Pthalimido-3-Fluoro-1-Propanol

A. Reaction of the title compound of Example 3 with potassium phthalimide and phthalimide Heat a mixture of the title compound of Example 3 (500 mg., 2.17 mmoles), and finely powdered potassium phthalimide (400 mg., 2.16 mmoles) and phthalimide (1.278 g., 8.69 mmoles) in dry DMF (dried over $P_2O_5$ and distilled under reduced pressure) with stirring in an oil bath under nitrogen at 93°-97° for 24 hrs. Cool the reaction mixture to room temperature and pour the cooled mixture into ice-cooled 0.1 M HCl (100 mL) and extract twice with dichloromethane (30 mL). Wash the combined extract successively with saturated sodium bicarbonate (30 mL) and water and then dry over anhydrous $Na_2SO_4$. Evaporate the solvent under vacuum to give a solid residue, and treat the solid with ethyl acetate-hexanes (10:1, v/v). Remove the precipitated solid by filtration and wash it with ethyl acetate-hexanes (10:1, v/v) (600 mg of phthalimide). Concentrate the filtrate and remove the precipitated solid as described above. Dissolve the residue in DMSO (1 mL) and apply the solution onto a column of silica gel (100 g.). Elute the column with ethyl acetate-hexanes (3:2, v/v). Evaporate the solvent to give a solid (438 mg.), and treat the solid with isopropyl alcohol. Remove the solid by filtration and wash it with isopropyl alcohol (yield 220 mg., 26.8%). Recrystallize the compound from isopropyl alcohol to give the title compound, colorless plates, m.p. 185°-187° (cf. D-(threo) isomer gave white needles from isopropyl alcohol;

m.p. 175°-177° C.), $R_f=0.027$ (solvent B) $v_{max}$(KBr): 3340 (OH), 1752 (symmetric C=O), 1685 (asymmetric C=O), 1587 (C=C) cm$^{-1}$; $^1$H nmr (CDCl$_3$-DMSO-d$_6$, 4:1, v/v)δ: 3.07 (s, 3H), 4.33 (ddd, 1H, $J_{3,F}=44.9$ Hz, $J_{3,3'}=8.9$ Hz, $J_{3,2}=4.0$ Hz), 4.67 (m, 1H, $J_{2,F}=16.5$ Hz, $J_{2,3}=4.0$ Hz, $J_{2,3'}=8.9$ Hz, $J_{2,1}=8.3$ Hz), 4.85 (dt, 1H, $J_{3',F}=45.8$ Hz, $J_{3,3'}=J_{3,2}=8.9$ Hz), 5.30 (d, 1H, $J_{1,2}=8.3$ Hz), 5.83 (OH) (bs, 1H), 7.64 (d, 2H, J=8.5 Hz), 7.76 (m, 4H), 7.88 (d, J=8.5 Hz).

B. Reaction of the title compound of Example 3 with anhydrous potassium fluoride and phthalimide Stir a mixture of the title compound of Example 3 and phthalimide (364 mg., 2.48 mmoles), and anhydrous potassium fluoride (Aldrich, 556 mg.) in dry DMF (4 mL.) at 90° in an oil bath for 35 hrs. Cool the reaction mixture to room temperature and dilute with dichloromethane. Pour the reaction mixture into water and separate the organic layer. Extract the aqueous layer with dichloromethane (10 mL). Wash the combined extracts with water and dry over anhydrous magnesium sulfate. Evaporate the solvent under vacuum give a solid, and treat the solid with ethyl acetate. Remove the solid by filtration and wash the solid with ethyl acetate. Evaporate the filtrate under vacuum to give a semisolid residue. Dissolve the residue in DMSO (1 mL) and apply the solution onto a column of silica gel (46 g.). Elute the column with the ethyl acetate-hexanes (3:2, v/v). Evaporate the eluant and isolate four compounds: phthalimide, unreacted starting material (26.0 mg.), unknown component A (24.6 mg.), and component B (104 mg.). The component B contained two to three compounds including the title compound (50%). Dissolve a portion (80 mg.) of this mixture (compound B) in hot isopropyl alcohol (3 mL) and cool the solution to room temperature and thence to 0°. A crystalline solid was removed by filtration and washed with cold isopropyl alcohol (22 mg., 15%). The compound had m.p., and ir and $^1$H NMR spectra, identical to those, respectively, of the title compound obtained in procedure (A) of Example 4.

EXAMPLE 5

D,L-(threo)-1-(4-Methylsulfonylphenyl)-2-Amino-3-Fluoro-1-Propanol

Dissolve hydroxylamine hydrochloride (460 mg.) in dry methanol (25 mL) (dried with Mg) with stirring. Add solid sodium methoxide (575 mg.) to the resulting solution and stir the mixture for 0.5 hr. Remove the precipitated solid by suction filtration. To the clear filtrate, add the title compound of Example 4 (500 mg., 1.32 mmoles). Stir the mixture for 19 hrs. at room temperature. Evaporate the solvent under vacuum and stir the resulting syrupy residue with an ice-cooled mixture of chloroform (10 mL), 30% NaOH solution (10 mL) and methanol (2 mL) until the residue completely dissolves. Separate the organic layer and extract the aqueous layer with chloroform (5×10 mL). Dry the combined chloroform extracts over anhydrous $Na_2SO_4$ and evaporate the solvent under vacuum to give a syrup which crystallized spontaneously (yield 381 mg. 97%). Recrystallize from methanol to give the title compound, white crystals;

m.p. 143°-144°, $R_f=0.22$ (solvent C), $v_{max}$ (KBr): 3330 and 3270 (NH$_2$), 3040 (OH), 1581 (NH$_2$) cm$^{-1}$; $^1$H NMR (CDCl$_3$-DMSO-d$_6$, 2:1, v/v) δ:1.46 (NH$_2$) (bs, 2H), 2.97-3.12 (m, 1H), 3.07 (s, 3H), 4.18 (ddd, 1H, $J_{3,F}=34.2$ Hz, $J_{3,3'}=9.0$ Hz, $J_{3,2}=5.9$ Hz), 4.41 (ddd, 1H, $J_{3',F}=34.2$ Hz, $J_{3',3}=9$ Hz, $J_{3',2}=5.9$ Hz), 4.71 (d, 1H, $J_{1,2}=4.2$ Hz), 5.53 (OH) (bs, 1H), 7.53 (d, 2H, J=8.1 Hz), 7.80 (d, 2H, J=8.1 Hz).

EXAMPLE 6

D,L-(threo)-1-(4-Methylsulfonylphenyl-2-Azido-3-Fluoro-1-Propanol

Heat a mixture of the title compound of Example 3 (500 mg., 2.17 mmoles), sodium azide (565 mg.), and ammonium chloride (465 mg) in dry DMSO (10 mL), with stirring, in an oil bath at 70° for 12 hrs. Pour the resulting reaction mixture into ice water and extract twice with dichloromethane (30 mL×2). Wash the combined extracts with water twice and dry the washed extracts over anhydrous sodium sulfate. Evaporate the solvent to give a syrup (491 mg.) and dissolve the resulting syrup with a small amount of dichloromethane. Add ether to the resulting solution. Collect a crystalline solid by filtration and wash it with ether to give the title compound (yield 164 mg., 27.6%);

m.p. 121°-123°, $R_f=0.33$ (solvent B); $v_{max}$ (KBr):3430 (OH), 2990, 2080 (N$_3$), 1585 (C=C) cm$^{-1}$;

$^1$H NMR (CDCl$_3$-DMSO-d$_6$, 4:1, v/v),δ:3.07 (s, 3H), 3.75 (m, 1H, J$_{2,1}$=5.2 Hz, J$_{2,3}$=6.8 Hz, J$_{2,3'}$=3.6 Hz, J$_{2,F}$=18.2 Hz), 4.31 (ddd, 1H, J$_{3,F}$=47.5 Hz, J$_{3,2}$=6.8 Hz, J$_{3,3'}$=10.0 Hz), 4.61 (ddd, 1H, J$_{3',F}$=45.3 Hz, J$_{3',2}$=3.6 Hz, J$_{3,3'}$=10.0 Hz), 4.90 (t, 1H, J$_{1,2}$=J$_1$,OH=5.2 Hz), 5.94 (OH) (d,1H, J$_{OH,1}$=5.2 Hz), 7.59 (d, 2H, J=8.1 Hz), 7.85 (d, 2H, J=8.1 Hz).

EXAMPLE 7

D,L-(threo)-1-(4-Methylsulfonylphenyl)-2-Amino-3-Fluoro-1-Propanol

Dissolve the title compound of Example 6 (100 mg.) in methanol (25 mL) and add 10% palladium-on-charcoal (16 mg.) in methanol (2-3 mL) to the solution. Shake the resulting mixture in a Parr apparatus under hydrogen at atmospheric pressure at room temperature for 1.5 hr. Remove catalyst by filtration and wash same with methanol. Evaporate solvent under vacuum to afford the title compound as a syrup (~90 mg.). The compound was essentially homogeneous on tlc, and was used in Example 8B without purification.

EXAMPLE 8

D,L-(threo)-1-(4-Methylsulfonylphenyl)-2-Dichloro-Acetamido-3-Fluoro-1-Propanol

A. Dissolve the title compound of Example 5 (208 mg., 0.841 mmoles) in methyl dichloroacetate (4 mL), triethylamine (0.1 mL) and dry methanol (1.6 mL). Reflux the resulting solution for 11 hrs. under nitrogen. Evaporate solvent under vacuum (0.5 mmHg) to give a syrup. Dissolve the syrup in dichloromethane and apply the resulting solution on to a column of silica gel (45 g.). Elute the column with ethyl acetate-hexanes (4:1, v/v) to give a solid 22 mg., 82%). Recrystallize the solid from a small amount of isopropyl alcohol and ether to give the title compound, white, fine crystals; m.p. 150°–151.5° (cf. D-(threo)-isomer; m.p. 151.5°–152°), R$_f$=0.48 (solvent D); ν$_{max}$ (KBr): 3450 (OH), 3300 (NH), 1669 (C=O), 1583 (C=C), 1511 (NH); $^1$H NMR (CDCl$_3$-DMSO-d$_6$, 4:1, v/v), δ: 3.02 (s,3H), 4.23-4.51 (m, 2H, H$_2$ and H$_3$), 4.60 (ddd, 1H, J$_{3'F}$=40.3 Hz, J$_{3',2}$=7.2 Hz, J$_{3,3'}$=8.9 Hz), 5.03 (dd, 1H, J$_{1,OH}$=5.0 Hz, J$_{1,2}$=1.4 Hz), 5.91 (OH) (d, 1H, J$_{OH,1}$=5.0 Hz), 6.17 (CHCl$_2$) (s,1H), 7.58 (d, 2H, 8.4 Hz), 8.19 (d, 2H, 8.5 Hz).

B. Dissolve the title compound of Example 7 (90 mg., 0.36 mmoles) in dry methanol (Mg. dried, 1.6 mL), triethylamine (0.1 mL) and methyl dichloroacetate (4 mL). Reflux the solution under nitrogen for 14 hrs. Evaporate solvent under vacuum to give a syrup. Chromatograph the syrup on a silica gel column, elute with ethyl acetate-hexanes (3:1, v/v) to give a solid after evaporation of the solvent (yield, 102 mg., 86.8%). Recrystallize the solid from isopropyl alcohol and ether to give the title compound as fine, white crystals, m.p. 148°–149° and having identical ir and $^1$H NMR spectra with those, respectively, of the dichloroacetamido derivative prepared from the phthalimide in accordance with procedure A of Example 8.

EXAMPLE 9

D-(threo)-(4-Methylsulfonylphenyl)-2-Amino-3-Fluoro-1-Propanol by resolution of D,L-(threo)1-(4-Methylsulfonylphenyl)-2-Amino-3-Fluoro-1-Propanol A. Resolution of (+)-(S)-O-methylmanclelic acid Heat 40.0 g. (0.241 moles) of racemic (+)-α-methyl-α-phenylacetic acid [D. G. Neilson et al. *J. Chem. Soc.*, (1962), 1519] with 40.0 g. (0.242 moles) of d-ephedrine (available from Aldrich) in 180 mL of 95% ethanol under reflux on a steam bath. Cool the resulting solution to room temperature slowly and leave undisturbed overnight (16 hrs.). Filter the resulting crystallized solid and wash same with 95% ethanol (20 mL) and ethyl ether to give 35.6 g. Recrystallize (twice) the solid from 95% ethanol to give 26.5 g. of salt of d-ephedrine and (+)-α-methoxy-α-phenylacetic acid [(+)-(S)-O-methylmandelic acid], m.p. 185°–188°, [α]$_D^{21}$+72.8° (c, 4.64, MeOH). Acidify 26.3 g. of the solid with 90 mL of ice-cooled sulfuric acid, with stirring to give a solution. Add sodium chloride (31 g.) and stir the resulting mixture. Add 100 mL of dichloromethane to the mixture to give a voluminous precipitate (ephedrine, sulfuric acid salt). Add another 100 mL portion of dichloromethane to the mixture and filter the mixture through a glass filter. Wash the solid with 100 mL of dichloromethane. Shake the filtrate and separate the organic and aqueous layers. Extract the aqueous layer with 100 ml of dichloromethane. Dry the combined organic layers over anhydrous magnesium sulfate. Evaporate the solvent to give an oil which solidifies on cooling to yield 13.2 g. of the title compound as a solid: m.p. 60.5°–62.0°, [α]$_D^{22}$+149° (C, 5.61, MeOH).

B. Formation of seed crystals of the salt of (+)-(S)-O-Methylmandelic acid and D-(threo)-1-(4-Methylsulfonylphenyl)-2-Smino-3-Fluoro-1-Propanol.

Dissolve (+)-(S)-O-Methylmandelic acid from Example 9, procedure A (44.9 mg., 0.270 mmole) and authentic D-threo-1-(4-methanesulfonylphenyl)-2-amino-3-fluoro-1-propanol (obtained by hydrolysis of the corresponding 2-dichloroacetamido derivative prepared in accordance with U.S. Pat. No. 4,311,857 using 33% HCl solution followed by treatment with 30% NaOH solution and extraction of the free base) (66.9 mg., 0.270 mmole) in n-butanol (1.5 mL) by warming on a steam bath. Cool the solution slowly to room temperature and leave the cooled solution undisturbed for 15 hrs. Filter the crystalline solid by filtration and wash the solid with an ether - n-butanol mixture (1:1, v/v) (2 mL) and ether (yield 84 mg.). Recrystallization gave fine needles of the title salt, m.p. 160°–161.5°, [α]$_D^{23}$+22.7° (c 11.8, MeOH); ν$_{max}$ (KBr): 3400, 3190, 2870, 2700, 2540, 1560, 1400, 1302 cm$^{-1}$.

C. Condition 1: Crystallizing the diastereomeric salt with stirring

Dissolve D,L-(threo)-1-(4-methylsulfonylphenyl)-2-amino-3-fluoro-1-propanol of Example 8 (1.193 g., 4.822 mmoles) and (+)-(S)-O-methylmandelic acid (0.8012 g, 4.822 mmoles) of Example 9A in n-butanol (25 mL) by warming on a steam bath. While the resulting solution is cooling to room temperature, seed the warm solution with an authentic sample of the salt (2 mg.) described in procedure (B) Example 9. Stir the mixture rigorously for 2 hrs. at room temperature. Remove the precipitated solid by filtration and wash the solid with an ice-cooled (1:1, v/v) n-butanol - anhydrous ether mixture (10 mL) and anhydrous ether, and then dry same under vacuum (0.5 mm Hg) overnight, yield 0.8540 g.; $[\alpha]_D^{21.2}+29.9°$ (c 8.36, MeOH). Recrystallize the partially resolved solid (0.8540 g.) from n-butanol (7 mL) to afford a solid (0.4566 g.), m.p. 155°–158.5° (softened at 150° C.),$[\alpha]_D^{23.5}+23.4°$ (c 7.72, MeOH).

Dissolve the salt (0.4566 g., 1.104 mmoles) in warm water (10 mL) and cool the resulting solution in an ice-water bath. Basify the cold solution by adding a 30% sodium hydroxide solution portionwise with stirring. Add sodium chloride (3 g.) and chloroform (20 mL) and stir the mixture. Remove a precipitate (sodium salt of the acid) by filtration and wash same with chloroform. Shake the filtrate and separate the organic layer. Extract the aqueous layer with chloroform (3×20 mL). Dry the combined extracts over anhydrous sodium sulfate. Concentrate the solution concentrated to give a syrup and dissolve same in absolute ethanol (5 mL). Filter the solution through a cotton plug. Evaporate the solvent to give a syrup. Remove the last traces of solvent from the syrup under vacuum to give a D-(threo)-1-(4-methylsulfonylphenyl)-2-amino-3-fluoro-1-propanol as a crystalline solid yield 0.2643 g.; $[\alpha]_D^{23}-33.6°$ (C 7.06, MeOH), m.p. 108.5°–110.0°; optical purity %: $-32.6°/-33.6°\times100=97.0\%$. The isolated free amine contained the D-(threo) enantiomer, the title compound, (98.5%) and the L-(threo) enantiomer (1.4%). The overall yield from the D,L-(threo)-1-(4-methylsulfanoylphenyl)-2-amino-3-fluoro-1-propanol was 0.264/0.569=44.1%.

D. Condition 2: Allowing crystallization of the diastereomeric salt to proceed without stirring Dissolve the title compound of Example 8 (1.4308 g., 5.784 mmoles) and (+)-(S)-O-methylmandelic acid of Example 9A (0.9611 g., 0.0611 g.) in hot n-butyl alcohol (20 mL) on a steam bath. Cool the solution to room temperature, and seed the turbid solution with the authentic salt described in procedure B of Example 9 and leave the seeded solution at room temperature without disturbance for 65 hrs. Collect the crystalline solid by filtration and wash the collected solid with an n-butanol and ether mixture (1:1, v/v) (10 mL) and ether (45 mL), and finally dry under vacuum, yield 1.4289 g.; $[\alpha]_D^{21.9}+35.9°$ (c 9.03, MeOH). Recrystallize the partially enriched solid (1.375 g.) from n-butanol (15 mL) as described above except leave same at room temperature for 24 hrs., yield 0.005 g.; $[\alpha]_D^{22.4}+31.7°$ (c 8.80, MeOH).

Recrystallize this solid (0.9118 g.) from n-butanol (10 mL) as described above to give a solid (yield 0.6951 g.), $[\alpha]_D^{22.2}+28.3°$ (c 9.00, MeOH). Recrystallize this material (0.6349 g.) from n-butanol (5 mL) to afford a solid (yield 0.5046 g.). $[\alpha]_D^{23.8}+26.4°$ (c 10.3, MeOH). Recrystallize the major portion of this solid (0.4433 g.) from n-butanol (4 mL) to give a solid (yield 0.2325 g.), m.p. 159°–161.5°,$[\alpha]_D^{23.0}+24.2°$ (c 9.95, MeOH). Decompose this salt (0.1800 g.) using sodium hydroxide solution as described in procedure B of this Example and isolate the title compound (yield 0.1013 g., 94.1%); $[\alpha]_D^{23.0}-32°$ (c 1.95, MeOH) cf. authentic sample of the title compound of this Example, $[\alpha]_D^{22}-35°$ (c 2.03, MeOH). Optical purity %: $-32°/-35°\times100=91\%$.

Racemic mixtures of the following D,L-(threo)-1-Aryl-2-amino-3-fluoro-1-propanols may be prepared using the appropriate reagents and thereafter resolved by fractional crystallization of their diastereomeric salts with the appropriate optically active acid in accordance with the procedures detailed hereinabove as well as the prior teachings of S. H. Wilen, in "Topics in Stereochemistry" ed by N. L. Allinger and E. L. Eliel, Vol. 6, p. 107 et seq., Wiley-Interscience, New York, 1971 and R. B. Woodward et al., *Tetrahedron*, Vol. 19 (1963) page 247 et seq. f157

What is claimed is:

1. A process for preparation of compounds represented by formula IVa and IVb:

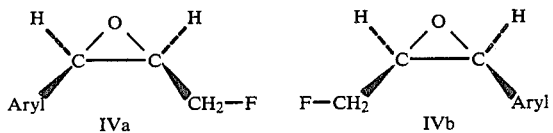

wherein Aryl is

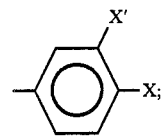

and wherein each of X and X' is independently $NO_2$, $SO_2R_1$, $SO_2NHR_1$, $OR_1$, $R_1$, CN, halogen, hydrogen, phenyl, or phenyl substituted by 1-3 halogens, $NO_2$, $SO_2R_1$, $R_1$ or $OR_1$; and wherein $R_1$ is lower alkyl; which comprises the following steps:

(a) contacting a 3-Aryl-2-propyn-1-ol with a fluorinating agent in an inert organic solvent to form 1-Aryl-3-fluoro-1-propyne;

(b) contacting the product of step (a) with a reagent selective for cis-hydrogenation to form a cis- 1-Aryl-3-fluoro-1-propene; and (c) contacting the product of step (b) with a peroxyacid to form the compounds represented by the formulas IVa and IVb.

2. The process of claim 1 wherein in step (a) the fluorinating agent is N-(1,1,2-trifluoro-2-chloroethyl)-N,N-diethylamine.

3. The process of claim 1 wherein Aryl is 4-methylsulfonylphenyl and wherein in step (b) the reagent selective for cis-hydrogenation comprises hydrogen, the Lindlar Catalyst and an aromatic amine compound.

4. The process of claim 1 wherein Aryl is 4-nitrophenyl and wherein in step (b) the reagent selective for cis-hydrogenation is diimide.

* * * * *